(12) United States Patent
Ahn et al.

(10) Patent No.: US 10,585,093 B2
(45) Date of Patent: Mar. 10, 2020

(54) BIO-SENSING DEVICE

(71) Applicant: FUZBIEN TECHNOLOGY INSTITUTE, INC., Rockville, MD (US)

(72) Inventors: Sae Young Ahn, Seoul (KR); Hyun Hwa Kwon, Gyeongsangbuk-do (KR)

(73) Assignee: NDD, INC., Gyeongsangbuk-Do (KR)

( * ) Notice: Subject to any disclaimer, the term of this patent is extended or adjusted under 35 U.S.C. 154(b) by 0 days.

(21) Appl. No.: 15/502,095

(22) PCT Filed: Nov. 29, 2016

(86) PCT No.: PCT/KR2016/013844
§ 371 (c)(1),
(2) Date: Feb. 6, 2017

(87) PCT Pub. No.: WO2017/116012
PCT Pub. Date: Jul. 6, 2017

(65) Prior Publication Data
US 2018/0113122 A1 Apr. 26, 2018

(30) Foreign Application Priority Data

Dec. 30, 2015 (KR) .................. 10-2015-0189628

(51) Int. Cl.
*G01N 33/543* (2006.01)
*G01N 33/68* (2006.01)
(Continued)

(52) U.S. Cl.
CPC ......... *G01N 33/5438* (2013.01); *C01G 39/06* (2013.01); *C07F 9/6571* (2013.01);
(Continued)

(58) Field of Classification Search
CPC .................. G01N 33/5438; G01N 27/4145
(Continued)

(56) References Cited

U.S. PATENT DOCUMENTS 5,270,556 A * 12/1993 Shimura ................ B82Y 10/00
257/192
2005/0048599 A1* 3/2005 Goldberg ................ B82Y 5/00
435/34
(Continued)

FOREIGN PATENT DOCUMENTS

CN 101520430 A 9/2009
CN 104345082 A 2/2015
(Continued)

OTHER PUBLICATIONS

Extended European Search Report dated Jun. 5, 2018, issued in connection with corresponding European Patent Application No. 16863188.5 (10 pages total).
(Continued)

*Primary Examiner* — Jill A Warden
*Assistant Examiner* — Jacqueline Brazin
(74) *Attorney, Agent, or Firm* — Mayer & Williams, PC; Stuart H. Mayer

(57) ABSTRACT

The present invention provides a bio-sensing device. The bio-sensing device includes an array of unit cells, each unit cell including: a source electrode and a drain electrode spaced apart from each other; a sensing film which is a channel between the source electrode and the drain electrode; and gate electrodes spaced apart from the sensing film, wherein the gate electrodes include an upper gate electrode and a lower gate electrode that are vertically spaced apart from each other.

11 Claims, 4 Drawing Sheets

(51) Int. Cl.
*C01G 39/06* (2006.01)
*C07F 9/6571* (2006.01)
*G01N 27/414* (2006.01)
*H01L 29/423* (2006.01)

(52) U.S. Cl.
CPC ......... *G01N 27/4145* (2013.01); *G01N 33/68* (2013.01); *H01L 29/4238* (2013.01)

(58) Field of Classification Search
USPC ....................................................... 422/82.02
See application file for complete search history.

(56) References Cited

U.S. PATENT DOCUMENTS

| | | | |
|---|---|---|---|
| 2005/0053524 A1* | 3/2005 | Keersmaecker | B82Y 10/00 422/88 |
| 2011/0244594 A1* | 10/2011 | Horii | G01N 33/54373 436/501 |
| 2013/0200438 A1 | 8/2013 | Liu et al. | |
| 2016/0202208 A1* | 7/2016 | Lee | G01N 27/4145 506/14 |
| 2017/0285017 A1* | 10/2017 | Ahn | G01N 33/5438 |

FOREIGN PATENT DOCUMENTS

| | | | |
|---|---|---|---|
| EP | 2017609 A1 | | 1/2009 |
| JP | 2006098187 | | 4/2006 |
| JP | 2010056303 A | | 3/2010 |
| JP | 2010-204126 A | | 9/2010 |
| JP | 2010204126 | * | 9/2010 |
| JP | 2010204126 A | | 9/2010 |
| KR | 10-2013-0038999 | | 4/2013 |
| KR | 20130038999 | * | 4/2013 |
| WO | 2015/001286 A1 | | 1/2015 |

OTHER PUBLICATIONS

Ahn et al., "Double-Gate Nanowire Field Effect Transistor for a Biosensor," NANO Letters, vol. 10, No. 8, pp. 2934-2938, Aug. 11, 2010 (5 pages total).

Howe, et al., "Functional inks of graphene, metal dichalcogenides and black phosphorus for photonics and ( opto ) electronics," Visual Communications and Image Processing; vol. 9553, Aug. 26, 2015 (17 pages total).

* cited by examiner

BIO-SENSING DEVICE

TECHNICAL FIELD

The present invention relates to a bio-sensing device, and more particularly, to a bio-sensing device having an electrode structure.

BACKGROUND ART

The test method used for the diagnosis of diseases is mainly based on coloration, fluorescence, etc. by enzyme reaction, but recently, immunoassay using immunity reaction between antigen and antibody has also been used. In the conventional immunoassay, the optical measurement method combining the optical label with the catalytic reaction of the enzyme was the most used. These methods have disadvantages in that they require a complicated procedure that can be performed mainly by a laboratory-oriented and skilled researcher, the apparatus for analysis is large and expensive, and the analysis takes a long time.

DETAILED DESCRIPTION OF THE INVENTION

Technical Problem

The present invention has been made to solve a lot of problems including the above ones, by providing a bio-sensing device that is capable of shortening analysis time and is relatively inexpensive. However, these problems are for illustrative purposes only, and the scope of the present invention is not limited thereto.

Technical Solution

There is provided a bio-sensing device according to an aspect of the present invention in order to solve the above-described problems. The bio-sensing device includes an array of unit cells, each unit cell including: a source electrode and a drain electrode spaced apart from each other; a sensing film which is a channel between the source electrode and the drain electrode; and gate electrodes spaced apart from the sensing film. Furthermore, the gate electrodes include an upper gate electrode and a lower gate electrode that are vertically spaced apart from each other.

In the bio-sensing device, the upper gate electrode and the lower gate electrode may be arranged to extend in a direction crossing each other without extending in parallel.

In the bio-sensing device, in order to prevent crosstalk between the array-arranged unit cells, only part of a gate voltage, at which a gate channel operation can be implemented, may be applied to the upper gate electrode, and only the remaining part of the gate voltage, at which the gate channel operation can be implemented, may be applied to the lower gate electrode.

In the bio-sensing device, in order to prevent crosstalk between the array-arranged unit cells, only half of a gate voltage, at which a gate channel operation can be implemented, may be applied to the upper gate electrode, and only the other half of the gate voltage, at which the gate channel operation can be implemented, may be applied to the lower gate electrode.

In the bio-sensing device, the material of the sensing film may include carbon nanotube (CNT), graphene, molybdenum disulfide (MoS2), or phosphorene.

In the bio-sensing device, a part of the source electrode or the drain electrode in contact with the carbon nanotubes, graphene, molybdenum disulfide, or phosphorene may have a comb-like shape.

In the bio-sensing device, the unit cell may further include a receptor that is attached to the sensing film and capable of binding to a target material.

In the bio-sensing device, the sensing film may be made of a material that can vary in resistance depending on the receptor and a target material bound to the receptor.

In the bio-sensing device, the receptor may be attached to the sensing film by a functional group and may be any one or more selected from the group consisting of an enzyme substrate, a ligand, an amino acid, a peptide, an aptamer, a protein, a nucleic acid, a lipid and a carbohydrate.

In the bio-sensing device, the functional group may be at least one selected from the group consisting of an amine group, a carboxyl group and a thiol group.

In the bio-sensing device, the target material may be at least one selected from the group consisting of a protein, a peptide, an aptamer, a nucleic acid, an oligosaccharide, an amino acid, a carbohydrate, a dissolved gas, a sulfur oxide gas, a nitrogen oxide gas, a residual pesticide, a heavy metal and an environmentally harmful substance.

The bio-sensing device may further include an upper substrate on which the sensing film and the upper gate electrode is formed; and a lower substrate on which the lower gate electrode, wherein the upper substrate and the lower substrate are vertically stacked and connected to each other.

Advantageous Effects

According to the embodiments of the present invention as described above, it is possible to provide a bio-sensing device that is capable of shortening analysis time and is relatively inexpensive. Of course, the scope of the present invention is not limited by these effects.

MODE OF THE INVENTION

Figure 1:
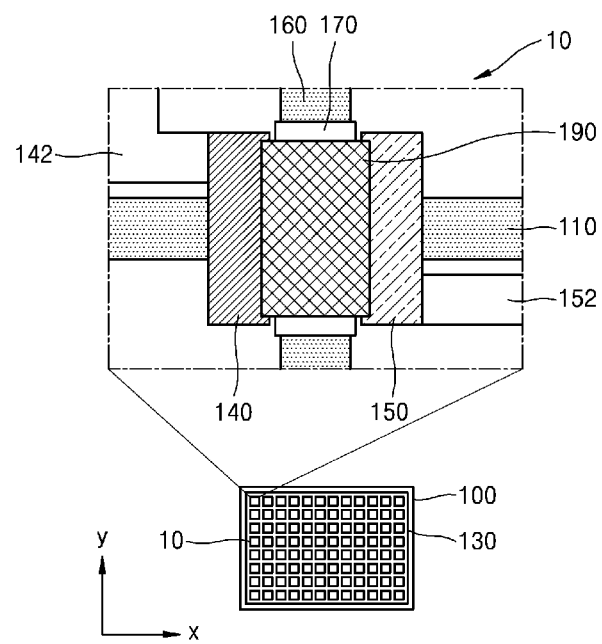
FIG. 1 is a schematic view illustrating a bio-sensing device and unit cells constituting the bio-sensing device according to an embodiment of the present invention.

Hereinafter, embodiments of the present invention will be described in detail with reference to the accompanying drawings. In the specification, it will be understood that when an element, such as a layer, region, or substrate, is referred to as being "on," "connected to," "stacked on" or "coupled to" another element, it can be directly "on," "connected to," "stacked on" or "coupled to" the other element or intervening elements may be present. In contrast, when an element is referred to as being "directly on," "directly connected to" or "directly coupled to" another element, there are no intervening elements present.

In the drawings, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. Furthermore, the thickness and size of each layer in the drawings may be exaggerated for convenience and clarity of explanation. Like numerals refer to like elements.

Figure 2:
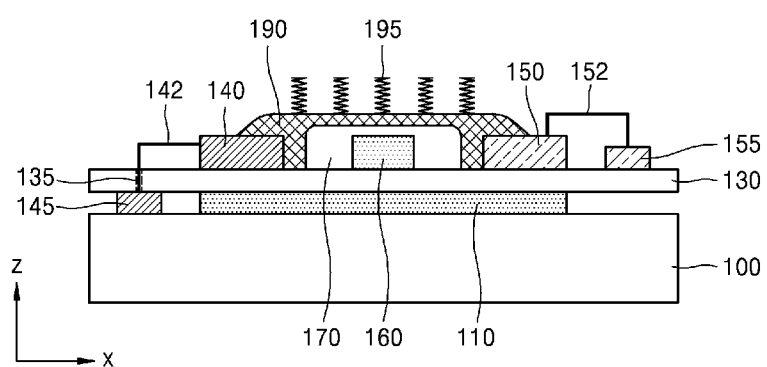
FIG. 2 is a schematic view illustrating a cross section of a unit cell constituting the bio-sensing device according to an embodiment of the present invention.
Figure 3:
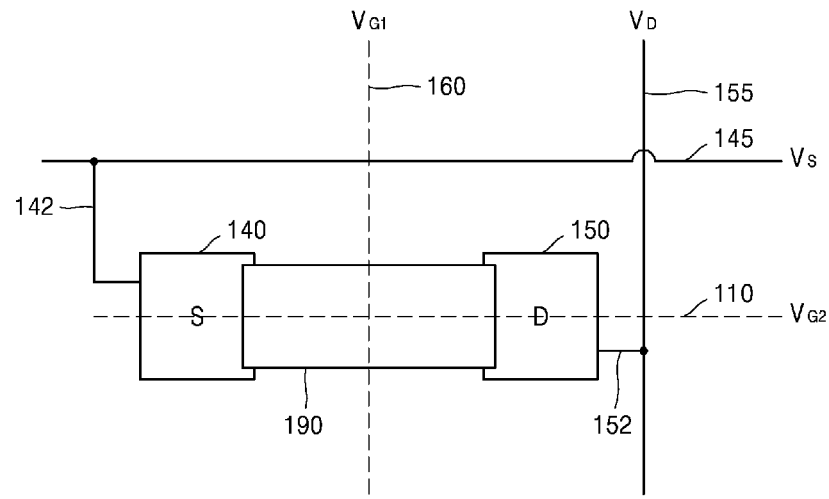
FIG. 3 is a circuit diagram schematically illustrating a circuit structure of a unit cell constituting the bio-sensing device according to an embodiment of the present invention.

FIG. 1 is a schematic view illustrating a bio-sensing device and unit cells constituting the bio-sensing device according to an embodiment of the present invention, FIG. 2 is a schematic view illustrating a cross section of a unit cell constituting the bio-sensing device according to an embodiment of the present invention, and FIG. 3 is a circuit diagram schematically illustrating a circuit structure of a unit cell constituting the bio-sensing device according to an embodiment of the present invention.

Referring to FIGS. 1 to 1 to 3, a bio-sensing device according to an embodiment of the present invention includes a unit cell 10 arranged in an array. The unit cell 10 includes a source electrode 140 and a drain electrode 150 spaced apart from each other, a sensing film 190 that serves as a channel between the source electrode and the drain electrode, and gate electrodes 110 and 160 spaced apart from the sensing film.

The unit cell 10 includes a receptor 195 that is attached to the sensing film 190 and capable of binding to a target material. The receptor 195 may be attached to the sensing film 190 by a functional group. For example, the receptor 195 may be any one or more selected from the group consisting of an enzyme substrate, a ligand, an amino acid, a peptide, an aptamer, a protein, a nucleic acid, a lipid and a carbohydrate. Meanwhile, the functional group may be at least one selected from the group consisting of, for example, an amine group, a carboxyl group and a thiol group. The target material may be selected from the group consisting of, for example, a protein, an aptamer, a peptide, a nucleic acid, an oligosaccharide, an amino acid, a carbohydrate, a dissolved gas, a sulfur oxide gas, a nitrogen oxide gas, a residual pesticide, a heavy metal and an environmentally harmful substance.

The sensing film 190 may be made of a material that can vary in resistance depending on the receptor 195 and a target material bound to the receptor. The material of the sensing film 190 may include, for example, carbon nanotube (CNT), graphene, molybdenum disulfide ($MoS_2$), or phosphorene. Meanwhile, in the bio-sensing device according to a modified embodiment of the present invention, the sensing film 190 may be made of a material that can vary in resistance by reacting directly with the target material without interposing the receptor 195.

The gate electrodes 110 and 160 are composed of an upper gate electrode 160 and a lower gate electrode 110 that are vertically spaced apart from each other. The upper gate electrode 160 located at the upper portion and the lower gate electrode 110 located at the lower portion may be arranged to extend in a direction crossing each other without extending in parallel. For example, the upper gate electrode 160 and the lower gate electrode 110 may be arranged to extend in directions perpendicular to each other.

The unit cell 10 constituting the bio-sensing device according to an embodiment of the present invention includes insulating members 130 and 170 interposed between the sensing film 190 and the gate electrodes 110 and 160. For example, the insulating member 170 may be interposed between the sensing film 190 and the upper gate electrode 160, and the insulating member 130 may be interposed between the sensing film 190 and the lower gate electrode 110. The insulating member 170 has, for example, the form of an insulating film, and the insulating member 130 may have the form of, for example, an insulating film or an insulating substrate.

The bio-sensing device according to an embodiment of the present invention can be used as an inspection device that is used for disease diagnosis and can be used as a sensing device that uses an immune reaction between an antigen and an antibody depending on the kind of a sensing film and a receptor. In this case, it is advantageous that, since the result of electrical measurement is utilized, a complicated procedure is not required in the analysis process, the apparatus for analysis is relatively inexpensive, and the analysis does not take a long time.

Referring further to FIG. 1, the number of unit cells 10 per substrates 100 and 130 is shown to be 8×12, i.e., 96 in total, but it is not limited thereto. If the size of the unit cell 10 is further reduced to nano size, the number of unit cells 10 may be increased to such as 4 times, 16 times, 64 times, 256 times, 1024 times, 4096 times, or 16384 times 8×12. Thus, by increasing the number of unit cells per substrate, the bio-sensing device of the present invention is capable of diagnosing various diseases and drastically reducing the inspection cost due to the shortened inspection time.

Figure 4A:
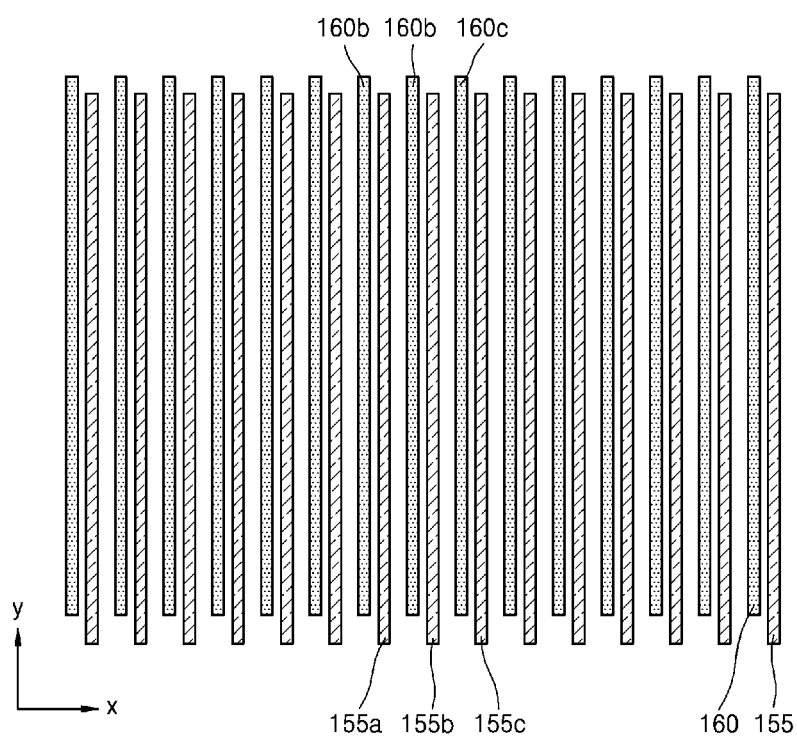
FIG. 4A is a schematic view illustrating a part of an upper layer of the bio-sensing device according to an embodiment of the present invention.
Figure 4B:
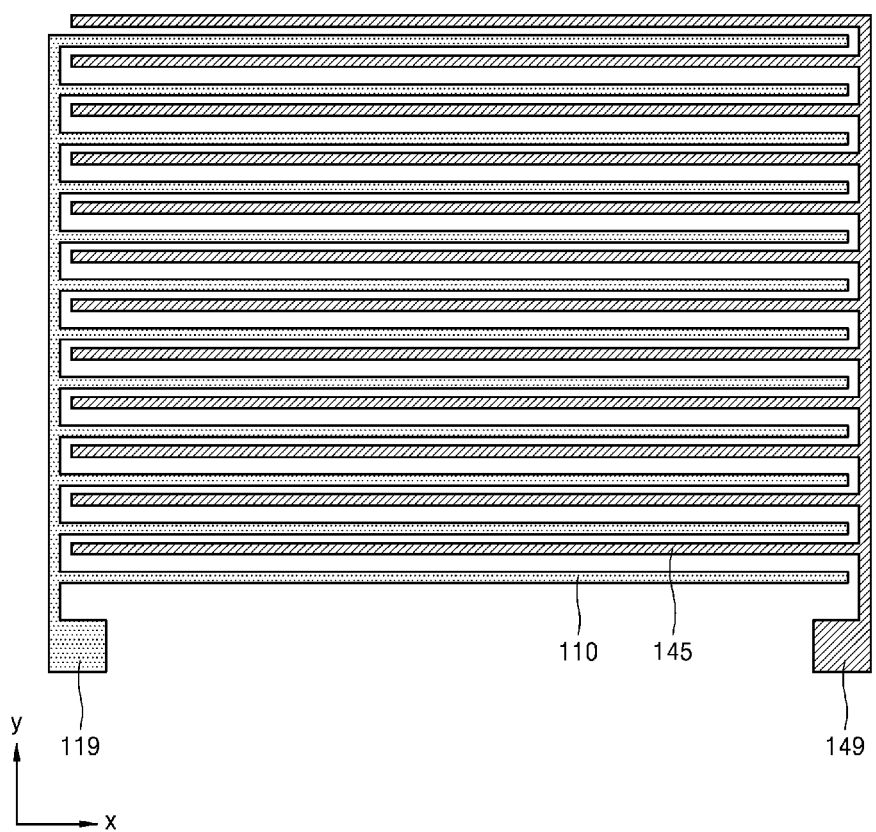
FIG. 4B is a schematic view illustrating a part of a lower layer of the bio-sensing device according to an embodiment of the present invention.

FIG. 4A is a schematic view illustrating a part of an upper layer of the bio-sensing device according to an embodiment of the present invention, and FIG. 4B is a schematic view illustrating a part of a lower layer of the bio-sensing device according to an embodiment of the present invention.

Referring to FIGS. 4A and 4B, the upper gate electrodes 160 extending in the first direction are arranged in parallel and spaced apart from each other, and the lower gate electrodes 110 extending in the second direction, which is a direction intersecting the first direction, are arranged in parallel and spaced apart from each other. The above-described unit cells 10 are formed in the respective regions where the upper gate electrodes 160 extending in the first direction and the lower gate electrodes 110 extending in the second direction cross each other.

Meanwhile, drain wiring lines 155 electrically connected to the drain electrode 150 are arranged to be spaced apart from each other while extending in parallel in the first direction on the upper layer where the upper gate electrodes 160 are disposed. Source wiring lines 145 electrically connected to the source electrode 140 are arranged to be spaced apart from each other while extending in parallel in the second direction on the lower layer where the lower gate electrodes 110 are disposed.

The upper gate electrodes 160 or the lower gate electrodes 110 may be commonly connected to each other and the drain wiring lines 155 or the source wiring lines 145 may be commonly connected to each other. For example, the lower gate electrodes 110 disposed on the lower layer may be commonly connected through the common terminal 119, and the source wiring lines 145 may be commonly connected through the common terminal 149.

As described above, in the bio-sensing device according to an embodiment of the present invention, as the unit cells 10 are arranged in an array, in order to prevent crosstalk between the array-arranged unit cells 10, only part $V_{G1}$ of the gate voltage $V_G$, at which the gate channel operation can be implemented, may be applied to the upper gate electrode 160 disposed at the upper portion, and only the remaining part $V_{G2}$ of the gate voltage $V_G$, at which the gate channel operation can be implemented, may be applied to the lower gate electrode 110 disposed at the lower portion ($V_G=V_{G1}+V_{G2}$).

For example, in order to prevent crosstalk between the array-arranged unit cells 10, only half ½·$V_G$ of the gate voltage $V_G$, at which the gate channel operation can be implemented, may be applied to the upper gate electrode 160 disposed at the upper portion and only the other half ½·$V_G$ of the gate voltage $V_G$, at which the gate channel operation can be implemented, may be applied to the lower gate electrode 110 disposed at the lower portion.

Here, since only half ½·$V_G$ of the gate voltage $V_G$, at which the gate channel operation can be implemented, is commonly applied to the lower gate electrodes 110 disposed at the lower portion commonly connected through the common terminal 119, the other half of the gate voltage $V_G$ must be applied to the upper gate electrode 160 in order to implement the gate channel operation. The other half of the gate voltage $V_G$ may be controlled such that it is applied to only one upper gate electrode 160b among the upper gate electrodes 160 disposed on the upper layer and is not applied to the upper gate electrodes 160a and 160c. When such an arrangement is employed, a gate channel operation is realized only in a series of unit cells that correspond to the upper gate electrode 160b, and is not realized in the adjacent unit cells that correspond to the upper gate electrodes 160a and 160c.

If the unit cells constituting the bio-sensing device according to an embodiment of the present invention employ a single gate structure instead of a vertically spaced apart double gate structure, a relatively high voltage may affect adjacent unit cells and a crosstalk phenomenon may occur in which a gate channel operation is unintentionally implemented in the adjacent cells. In the present invention, the crosstalk phenomenon can be prevented by arranging the gate electrodes constituting the unit cells to be vertically spaced apart from each other and by applying the divided gate voltages.

Figure 5:
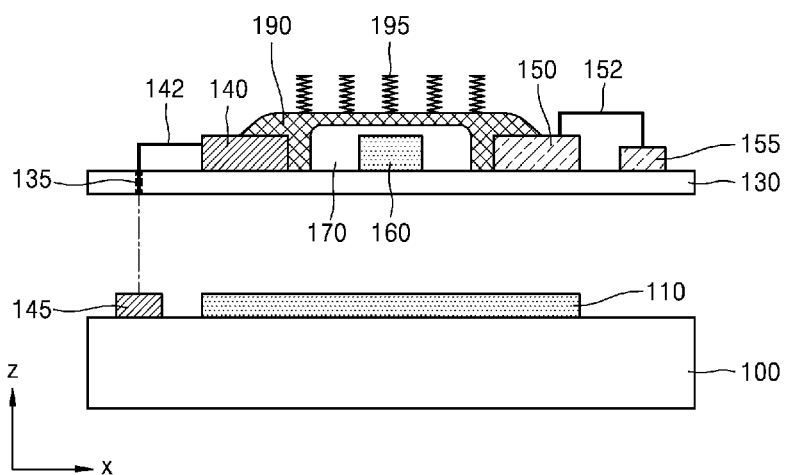
FIG. 5 is a view illustrating an example of manufacturing a unit cell constituting the bio-sensing device according to an embodiment of the present invention.

FIG. 5 is a view illustrating an example of manufacturing a unit cell constituting the bio-sensing device according to an embodiment of the present invention.

Referring to FIG. 5, in order to provide the unit cell structure of FIG. 2, a lower structure having the source wiring lines 145 and the lower gate electrode 110 formed on the lower substrate 100 is prepared. Then, an upper structure having the drain wiring lines 155 and the upper gate electrode 160 formed on the upper substrate 130 is prepared. Then the upper structure is stacked on and connected to the lower structure. The lower substrate 100 of the lower structure may also serve as a support for the bio-sensing device. The upper substrate 130 may also serve to insulate the sensing film 190 from the lower gate electrode 110 and may include a through-hole 135 through which a connection pattern 142 for electrically connecting the source electrode 140 and the source wiring line 145 may pass. The upper substrate 130 may be a PCB substrate having a thickness of about 0.1 mm, and the lower substrate 100 may be a PCB substrate having a thickness of about 1 mm. The bio-sensing device according to an embodiment of the present invention can easily provide a complicated double gate electrode structure at a relatively low cost by employing the above-described double substrate structure.

Figure 6:
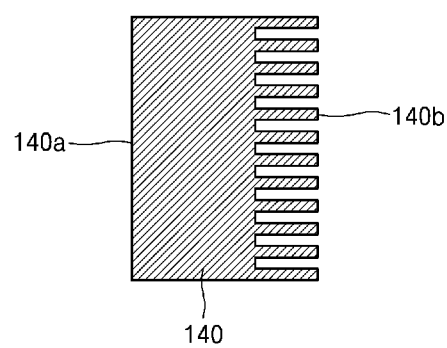
FIG. 6 is a view illustrating a shape of a source electrode in a unit cell constituting the bio-sensing device according to an embodiment of the present invention.

FIG. 6 is a view illustrating a shape of a source electrode in a unit cell constituting the bio-sensing device according to an embodiment of the present invention.

Referring to FIG. 6, in the source electrode 140, a region 140b in contact with the sensing film 190 such as carbon nanotubes, graphene, molybdenum disulfide, or phosphorene may have a comb-like shape. According to this structure, the bonding force or interconnectivity between the sensing film 190 and the source electrode 140 can be improved. Likewise, in the drain electrode, a region in contact with the sensing film such as carbon nanotube or graphene may have a comb-like shape, thereby improving the bonding force or interconnectivity between the drain electrode and the sensing film.

While the present invention has been particularly shown and described with reference to embodiments shown in the drawings, it is only for illustrative purposes. It will be understood by those skilled in the art that various modifications and equivalent embodiments may be made. Therefore, the scope of the present invention should be determined by the technical idea of the appended claims.

The invention claimed is:

1. A bio-sensing device comprising:
an array of unit cells, each unit cell including:
a source electrode and a drain electrode spaced apart from each other;
a sensing film that serves as a channel between the source electrode and the drain electrode; and
gate electrodes spaced apart from the sensing film,
wherein the gate electrodes include an upper gate electrode and a lower gate electrode that are vertically spaced apart from each other,
wherein the upper gate electrode is disposed above the lower gate electrode, and the sensing film is disposed above the upper gate electrode, and
wherein the upper gate electrode and the lower gate electrode are arranged to extend in a direction crossing each other without extending in parallel.

2. The bio-sensing device of claim 1, wherein, in order to prevent crosstalk between the unit cells, only part of a gate voltage, at which a gate channel operation can be implemented, is applied to the upper gate electrode, and only the remaining part of the gate voltage, at which the gate channel operation can be implemented, is applied to the lower gate electrode.

3. The bio-sensing device of claim 1, wherein, in order to prevent crosstalk between the unit cells, only half of a gate voltage, at which a gate channel operation can be implemented, is applied to the upper gate electrode, and only the other half of the gate voltage, at which the gate channel operation can be implemented, is applied to the lower gate electrode.

4. The bio-sensing device of claim 1, wherein the sensing film is made of a material selected from the group comprising of carbon nanotube (CNT), graphene, molybdenum disulfide ($MoS_2$), or phosphorene.

5. The bio-sensing device of claim 4, wherein a part of the source electrode or the drain electrode in contact with the carbon nanotubes, graphene, molybdenum disulfide, or phosphorene has a comb-like shape.

6. The bio-sensing device of claim 1, wherein the unit cell further includes a receptor that is attached to the sensing film and capable of binding to a target material.

7. The bio-sensing device of claim 6, wherein the sensing film is made of a material that varies in resistance depending on the receptor and a target material bound to the receptor.

8. The bio-sensing device of claim 6, wherein the receptor is attached to the sensing film by a functional group and is selected from the group consisting of an enzyme substrate, a ligand, an amino acid, a peptide, an aptamer, a protein, a nucleic acid, a lipid and a carbohydrate and the combinations thereof.

9. The bio-sensing device of claim 8, wherein the functional group is at least one selected from the group consisting of an amine group, a carboxyl group and a thiol group.

10. The bio-sensing device of claim 6, wherein the target material is a protein or a peptide.

11. The bio-sensing device of claim 1, further comprising:
an upper substrate on which the sensing film and the upper gate electrode is formed; and
a lower substrate on which the lower gate electrode is formed,
wherein the upper substrate and the lower substrate are vertically stacked and connected to each other.

* * * * *